US007500957B2

(12) United States Patent
Bledsoe

(10) Patent No.: US 7,500,957 B2
(45) Date of Patent: Mar. 10, 2009

(54) MUSCLE POWERED DYNAMIC KNEE BRACE

(75) Inventor: Gary R. Bledsoe, Mansfield, TX (US)

(73) Assignee: Medical Technology, Inc., Grand Prairie, TX (US)

( * ) Notice: Subject to any disclaimer, the term of this patent is extended or adjusted under 35 U.S.C. 154(b) by 569 days.

(21) Appl. No.: 10/774,657

(22) Filed: Feb. 5, 2004

(65) Prior Publication Data

US 2005/0177082 A1   Aug. 11, 2005

(51) Int. Cl.
  *A61F 13/00*  (2006.01)
(52) U.S. Cl. .............................. 602/26; 602/16; 602/23
(58) Field of Classification Search ............... 602/5, 602/20, 23, 26, 27, 16; 128/877, 878, 879
   See application file for complete search history.

(56) References Cited

U.S. PATENT DOCUMENTS

| | | | |
|---|---|---|---|
| 1,381,290 | A | 6/1921 | Diadul, Jr. |
| 3,902,482 | A | 9/1975 | Taylor |
| 4,256,097 | A | 3/1981 | Willis |
| 4,463,751 | A | 8/1984 | Bledsoe |
| 4,817,588 | A | 4/1989 | Bledsoe |
| 4,856,501 | A | 8/1989 | Castillo et al. |
| 4,881,532 | A | 11/1989 | Borig et al. |
| 4,955,369 | A | 9/1990 | Bledsoe et al. |
| 5,056,509 | A | 10/1991 | Swearington |
| 5,131,385 | A | 7/1992 | Kuehnegger et al. |
| 5,277,698 | A | 1/1994 | Taylor |
| 5,302,169 | A | 4/1994 | Taylor |
| 5,400,806 | A | 3/1995 | Taylor |
| 5,662,596 | A | 9/1997 | Young |
| 5,766,140 | A | 6/1998 | Tillinghast, III et al. |
| 5,788,618 | A | * 8/1998 | Joutras ...................... 482/114 |

FOREIGN PATENT DOCUMENTS

| | | |
|---|---|---|
| DE | 357243 | 8/1922 |
| DE | 846895 | 8/1952 |
| DE | 2239382 | 2/1974 |
| GB | 2136294 A | 9/1984 |

(Continued)

OTHER PUBLICATIONS

Komistek, Richard D. et al., "An In Vitro Analysis of the Effectiveness of the Osteoarthritic Knee Brace During Heel Strike of Gait," 1999, 12 pages, vol. 14, No. 6, Journal of Arthroplasty (printed from Bledsoe Brace Systems web site: http://bledsoebrace.com/studies/rose.htm).

(Continued)

*Primary Examiner*—Kim M Lewis
(74) *Attorney, Agent, or Firm*—James E. Walton

(57) ABSTRACT

A dynamic knee brace that can be used to apply a bending force across the knee. Two brace arms are connected together by a central joint that allows the knee to pivot. A joint in each brace arm allows the brace arm to be inclined toward the leg. A cam assembly is present to actively incline each brace arms toward the leg as the knee moves to full extension. An adjustment mechanism for the cam assemblies provides control over the maximum amount of inclination each brace arm achieves. Preferably, the adjustment mechanism adjusts the cams equally so that both brace arms are inclined by the same amount.

37 Claims, 5 Drawing Sheets

FOREIGN PATENT DOCUMENTS

GB         2163352 A     2/1986

OTHER PUBLICATIONS

Hewett, Timothy E. et al., "Decrease in Knee Joint Pain and Increase in Function in Patients With Medial Compartment Arthrosis: A Perspective Analsysis of Valgus Bracing," 1998, 16 pages, vol. 21, No. 2, Orthopedics (printed from Bledsoe Brace Systems web site: http://bledsoebrace.com/studies/cinci.htm).

Bledsoe Thruster Knee Brace brochure (CP010156) and Application Instructions (CP00020138), 4 pages, Nov. 1995.

Bledsoe Aligner Brace brochure and Application Instructions (CP020305, Rev. B), 5 pages, Mar. 2001.

* cited by examiner

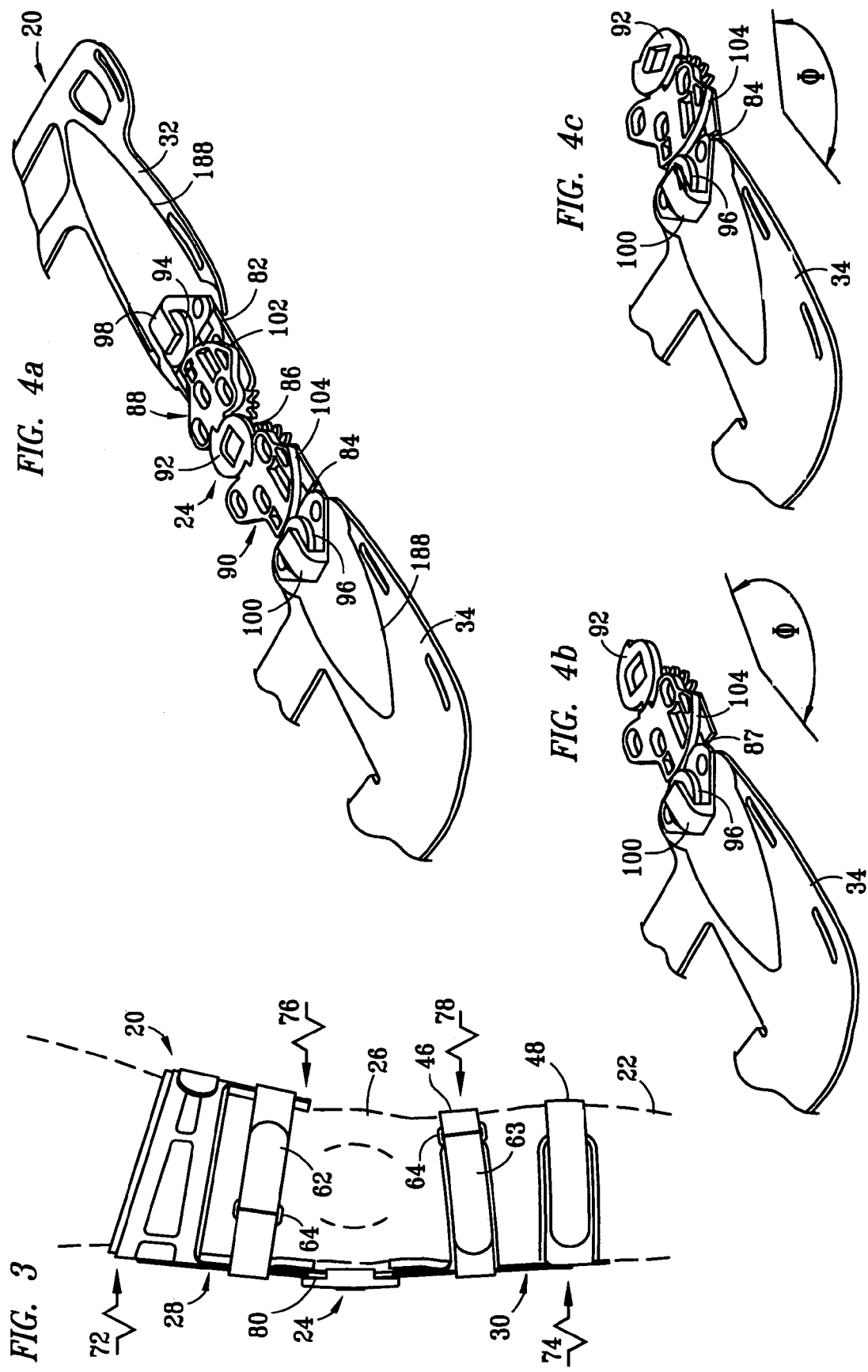

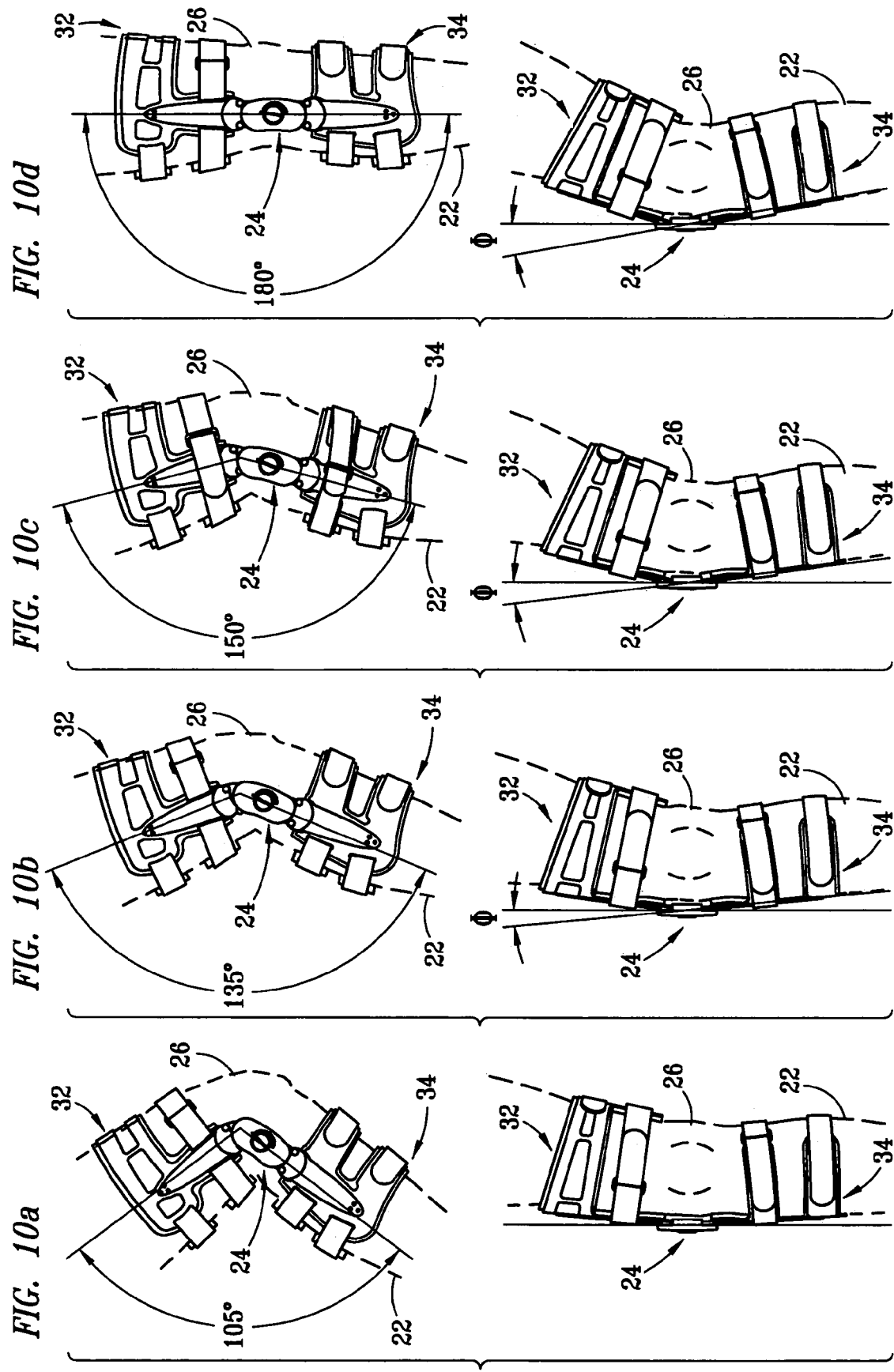

MUSCLE POWERED DYNAMIC KNEE BRACE

BACKGROUND OF THE INVENTION

1. Field of the Invention

This invention relates generally to orthopedic knee braces and, more particularly, to a dynamic knee brace that uses muscle power to apply a bending force across a knee.

2. Description of Related Art

Unicompartmental osteoarthritis is a condition where the cartilage on one compartment of the knee has worn away more than the other compartment. This damage to the compartment on one side of the knee causes increased pressure on the damaged compartment, which may be severe enough to be visible as a change in the angulation of the joint. This makes it painful for the patient to engage in activities where there is a load being applied to the knee, such as waking or even standing. Unicompartmental osteoarthritis is generally treated by shifting the load applied across the knee to the compartment that has the least amount of damage, thereby opening the damaged compartment.

If there is also a deformity in the knee joint, a high tibial osteotomy can be used to realign the joint and shift the load to the undamaged compartment in the knee. A high tibial osteotomy is a surgical procedure that involves cutting a triangular section off the top of the tibia to realign the joint and open the damaged compartment. After this procedure, it is important to protect the leg to ensure that the bones heal together properly. This is often accomplished by placing the leg in a cast. However, since it is beneficial to allow the knee to pivot during the healing process, a brace can be used to hold the leg in the desired configuration while allowing the knee to freely pivot. If a brace is used after a high tibial osteotomy, the brace arms are often bent to the desired inclination to hold the leg in the desired configuration and provide the necessary support.

A knee brace may also be used without surgery, in order to treat unicompartmental osteoarthritis. This is accomplished by providing a bending force across the knee to hold open the damaged compartment of the knee. A three-point bending force is accomplished by having a force applied to the knee on the side opposite from the damaged compartment. This is often done using a strap, a condoyle pad, or other such instrumentality. The force against the knee is countered by two brace arms, which provide static forces against the leg above and below the knee. The brace arms can be bent or otherwise inclined toward the leg using known joints in order to increase the force across the knee. By pulling the knee against the brace arms, the brace applies a three-point bending force at the knee to open the damaged compartment. Alternatively, a four-point bending force can be utilized by applying a force just above and below the knee instead of applying a single force directly to the knee. This avoids applying pressure directly at the knee but creates an equivalent bending moment at the knee as a three-point bending force.

A major disadvantage of most braces for treating unicompartmental osteoarthritis is that they provide a static bending force across the knee, which does not change as the knee moves between flexed and extended positions. The pressure in the damaged compartment increases, thereby causing pain, only when weight is being applied to the leg. This occurs close to or at full extension of the knee. The application of force when the knee is partially flexed can make the brace uncomfortable to wear. In addition, when the knee is partially flexed applying a bending force across the knee results in a rotational force that results in a tendency of the brace to rotate around the leg, which lessens its effectiveness. This tendency to rotate increases with the amount of force applied, thereby preventing static force braces from applying the forces required to treat more severe cases of unicompartmental osteoarthritis.

Applicant has previously provided a dynamic brace that overcomes this problem, called the Thruster brace, which has been successfully marketed by Medical Technology, Inc. of Grand Prairie, Tex. The Thruster brace only applies the bending force as the knee nears full extension and completely removing it as the knee bends back to a flexed position. It has two brace arms that are connected together by a central polycentric joint that allows the knee to pivot. A hinge in each brace arm allows each brace arm to incline in a medial/lateral direction. Two cams are positioned over the central joint with cam surfaces facing each other and cam followers on the other end of each cam. As the knee moves to extension, the cam surfaces on each assembly contact and roll along each other, and due to the shape of the cams, push the corresponding cam followers away from the central joint.

At some point as the knee moves to full extension, the cam followers contact the end of a timing screw extending from an adjustment block located on each brace arm. Further extension of the knee pushes the cam follower further toward the adjustment block, resulting in the brace arm being pushed around the medial/lateral joint toward the leg into a particular degree of inclination. The timing of when the cam follower first contacts the adjustment block, and thus the total amount of inclination that is achieved at full extension, is determined by how far the adjustment screw is threaded through each of the adjustment blocks. While this brace has achieved significant results, there is still opportunity for improvement of dynamic braces.

SUMMARY OF THE INVENTION

A dynamic knee brace that can be used to apply a bending force across the knee. Two brace arms are connected by a central joint that allows the knee to pivot. A joint in each brace arm allows the brace arm to be inclined in the medial/lateral plane. A cam assembly actively and dynamically inclines each brace arms toward the leg as the knee moves from flexion to full extension. An adjustment mechanism for the cam assemblies provides control over the timing of the dynamic force and thus the maximum amount of inclination each brace arm achieves at full extension. Preferably, the adjustment mechanism adjusts the cams equally so that both brace arms are inclined by the same amount, regardless of the adjustment used.

BRIEF DESCRIPTION OF THE DRAWINGS

A preferred embodiment of the present invention is further described and explained in relation to the following figures wherein:

FIG. 3 is a front elevation view of the preferred embodiment of the current invention in place on a patient's leg and at full extension with the brace arms in a partially loaded state, showing the forces applied to the leg by the brace;

FIG. 4a is an expanded and partially cut away view showing the interaction between the adjustment wheel and the travel cams when the brace is completely unloaded and at full extension;

FIG. 4b shows the joint depicted in FIG. 4a when the adjustment wheel is adjusted to move the travel cams radially outward, thereby inclining the brace arms;

FIG. 4c shows the joint depicted in FIG. 4a when the adjustment wheel is adjusted so that the travel cams are at their maximum distance from each other, thereby providing the maximum amount of inclination of the brace arms;

FIG. 10a is a perspective view of the preferred embodiment on a leg and adjusted, with the knee at 105° and the brace arms not inclined;

FIG. 10b is a perspective view of the brace in 10a when the knee is extended to 135°;

FIG. 10c is a perspective view of the brace in 10a when the knee is extended to 150°; and FIG. 10d is a perspective view of the brace in 10a when the knee is fully extended.

DETAILED DESCRIPTION OF THE PREFERRED EMBODIMENT

A brace according to a preferred embodiment of the present invention is adapted to be secured around the leg of a patient, use muscle power to provide the required amount of bending force across the knee as the knee moves to full extension, and to dynamically remove the force as the knee flexes. While the following description of the preferred embodiment relates to a brace for treating the medial compartment of the left leg, one of skill in the art would understand any minor alterations required to adapt the preferred embodiment of the current invention for the treatment of the medial or lateral compartment of either knee.

Figure 2:
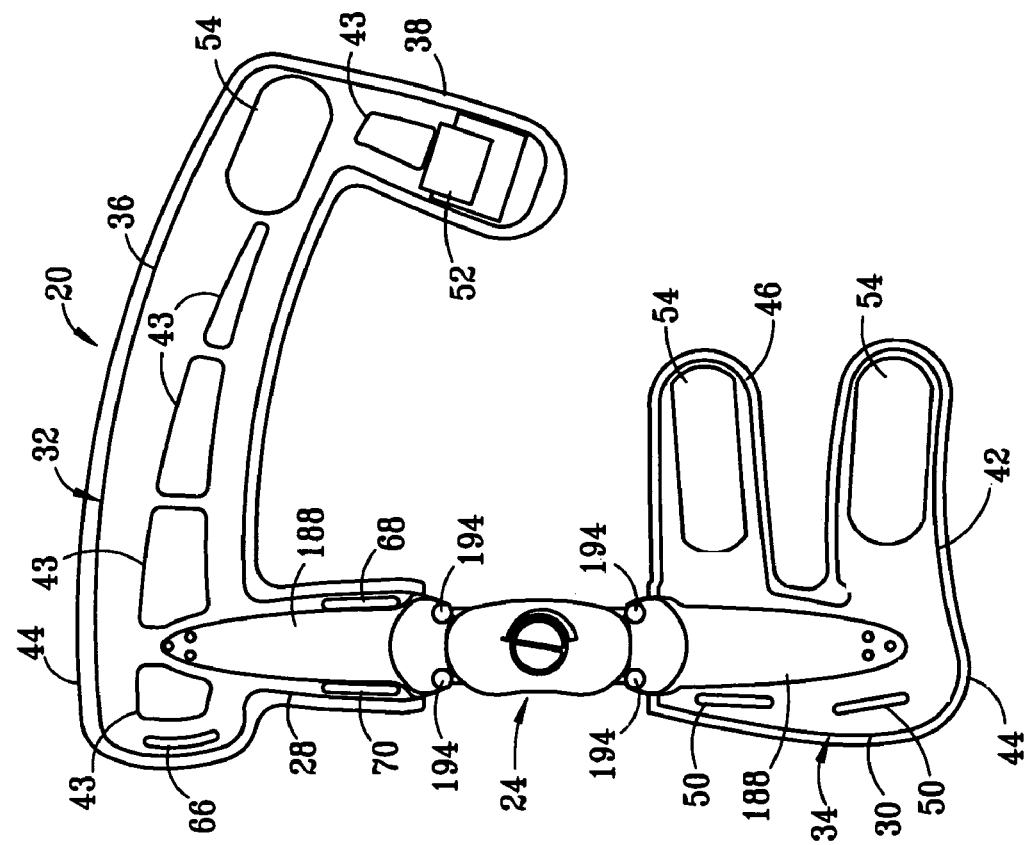
FIG. 2 is a side elevation view of the preferred embodiment of the current invention with all of the straps and pads removed and the shells flattened out for clarity.
Figure 1:
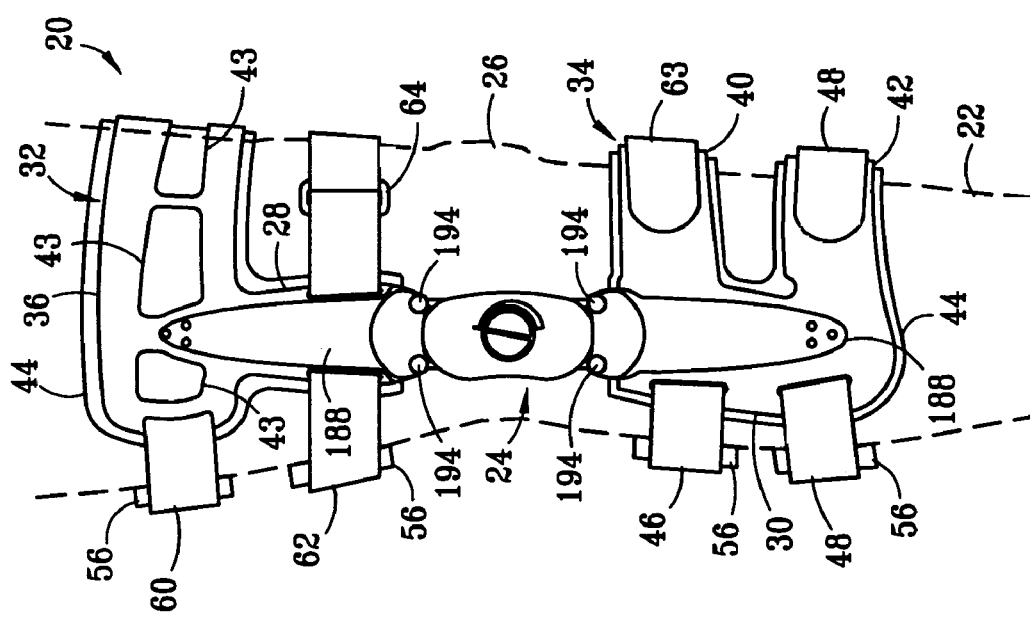
FIG. 1 is side elevation view of a preferred embodiment of the current invention in place on a patient's leg with the brace arms in a completely unloaded state.

With respect to FIGS. 1 and 2, brace 20 is adapted to be located about leg 22 such that joint 24 is next to the compartment of knee 26 that is damaged and needs to be opened. Upper shell 32 is located against leg 22 above knee 26 and lower shell 34 is located against leg 22 below knee 26. Upper shell 32 is secured to media/lateral joint 82 through the use of rivets 194 and lower shell 34 is likewise secured to media/lateral joint 84 shown in FIGS. 4a and 4c. Upper shell 32 is made up of upper brace arm 28 extending up leg 22, wrap 36 that extends around the front of leg 22, and extension 38 that extends down leg 22 toward knee 26 opposite from joint 24. Lower shell 34 is composed of lower brace arm 30 extending down leg 22 and fingers 40 and 42 that extend partially around the front of leg 22. Pads 44 are preferably located on the inside of shells 32 and 34 to provide a more comfortable fit against leg 22. Pads 44 are preferably secured to shells 32 and 34 through the use of a hook and loop fastening system, e.g. Velcro. The hook portion of the fastening system secured to the inside of shells 32 and 34 grip the pile surface of pads 44 that make up the loop portion of the fastening system. Upper shell 32 also has openings 43 through which pads 44 are visible. Openings 43 allow moisture to escape from under shell 32 without weakening the structure of shell 32. Kneepad 80 shown in FIG. 3, located on the inside of joint 24, cushions knee 26 and is secured to joint 24 by hook strip 52 on the interior of joint 24.

Shells 32 and 34, which include brace arms 28 and 30, are preferably composed of an aluminum alloy that has a significant amount of flex in it. While brace arms 28 and 30 may be completely rigid, it is preferred that there is a degree of flex in them to enhance the thrust that is applied by brace 20 while eliminating point pressure. If, brace arms 28 and 30 are made rigid, it is desirable that some other structure is provided so that shells 32 and 34 lay flat against leg 22 at the points where forces 72 and 74 are applied, in order to avoid the creation of point pressures. Extensions 188 runs along brace arms 28 and 30 help transmit forces along brace arm 28 and 30 so that forces 72 and 74 are applied to leg 22 as shown in FIG. 3. They also enable brace arms 28 and 30 to be made of a thinner material to increase their overall flexibility, while providing the necessary thickness to brace arms 28 and 30 only where necessary to transmit forces along brace arms 28 and 30.

Straps 46 and 48 secure lower shell 34 to leg 22. At one end, straps 46 and 48 pass through slots 50 in shell 34 and are secured back upon themselves using Velcro. For strap 48, the other end is secured to pile surfaces 54 on fingers 42 using a Velcro strip. For strap 46, the other end passes through D-ring 64 and is secured back upon itself using Velcro. Web 63 also passes through D-ring 64, is sewn back upon itself and the other end of web 63 is secured to pile surface 54 on finger 40. The use of D-ring 64 on strap 46 allows strap 46 to be adjusted in length to accommodate leg 22 of varying sizes while the use of web 63 allows strap 46 to be quickly released when removing brace 20 from leg 22. Pads 56 are secured on the interior of straps 46 and 48 opposite from shell 34 using hook strips (not shown). In addition, there is elastic section in strap 48 that keeps strap 48 snug while the muscles in leg 22 contract and relax, which changes the circumference of leg 22 to some extent. In cases where the musculature of leg 22 is insufficient to hold brace 20 in place alone, an ankle-foot orthosis, as is well known in the art, can be secured to lower brace arm 30 to help hold brace 20 in the desired position.

Strap 60 similarly passes through slot 66 in upper shell 32 and is secured back upon itself using Velcro. The other end of strap 60 is secured to pile surface 54 at the end of wrap 36 on upper shell 32, also using Velcro. Strap 60 also has an elastic similar to strap 48. Pad 56 is secured to the inside of strap 60 opposite from upper shell 32 using Velcro. One end of strap 62 passes through D-ring 64 and is sewn back upon itself. Strap 62 then passes through slot 68 in upper shell 32, behind upper brace arm 28 and back out slot 70. Strap 62 then passes behind leg 22, around extension 38 and back around leg 22 to pass through D-ring 64 and be secured back upon itself in front of leg 22 using Velcro. Pad 56 is secured on the inside of strap 64, behind leg 22 and between upper brace arm 28 and extension 38. There is also hook strip 52 secured to the bottom of extension 38 that secures to the pile surface of strap 64 and holds it in the desired location.

As can be seen in FIG. 3, when joint 24 is adjusted to generate a bending force and knee 26 is at or near full extension, a bending force is created across knee 26. As can be better seen in FIG. 10d, joint 24 inclines both upper brace arm 28 and lower brace arm 30 an angle θ from vertical as knee 26 moves from flexion to full extension. As a result, upper brace arm 28 and lower brace arm apply forces 72 and 74 respectively to leg 22. On the other side, the bottom end of extension 38, aided by strap 62, applies force 76 to leg 22 and strap 46 applies force 78 to leg 22. Forces 76 and 78 on one side combine with forces 72 and 74 on the other side to create a four-point bending force across knee 26 that shifts the compressive force passing through knee 26, to the compartment of the knee that is further away from joint 24, thereby relieving pressure passing through, and in some cases opening, the damaged compartment of knee 26.

It is recognized that due to the flexible nature of the shells 32 and 34, brace arms 28 and 30 will not remain straight and thus will not take on a defined angle of inclination. Rather brace arms 28 and 30 will flex such that while the inclination of the portion of brace arms 28 and 30 will change to some extent, the remainder of brace arms 28 and 30 will flex such that shell 32 and 34 remain flat against leg 22 so that no point pressures develop. Use of the term "inclination" in connection with this invention is intended to also encompass this situation where the brace arms are rotated around the medial/lateral joints toward the leg but there is no defined angle of inclination of the brace arm due to the flexibility of brace arms 28 and 30.

With respect to FIG. 4, joint 24 is generally composed of medial/lateral joints 82 and 84 in brace arms 28 and 30 respectively, central joint 86, adjustment wheel 92 positioned over central joint 86, travel cams 88 and 90 that extend from adjustment wheel 92 toward medial/lateral joints 82 and 84 respectively, and stop blocks 98 and 100. Wheels 94 and 96 are pivotally secured in stop blocks 98 and 100, which are adjacent to medial/lateral joints 82 and 84. Wheels 94 and 96 also project over medial/lateral joints 82 and 84 toward central joint 86. Cams 88 and 90 have cam surfaces 102 and 104 on their edge closest to wheels 94 and 96. Cam surfaces 102 and 104 are each an arcuate surface with an increasing radius from one end to the other.

As knee 24 moves to full extension, at some point roller wheels 94 and 96 contact cam surfaces 102 and 104 respectively and roll along cam surfaces 102 and 104 until they reach the position depicted in FIGS. 4a-c. Wheels 94 and 96 are pivotally connected to stop blocks 98 and 100 and are adapted to roll along cam surfaces 102 and 104 to provide a smoother motion than if stop blocks 98 and 100 simply slid along cam surfaces 102 and 104. Cam surfaces 102 and 104 have an arcuate curve such that the radial distance from cam surface 102 and 104 to contact surface 120 gets progressively larger from one end of cam surfaces 102 and 104 to the other. As knee 26 moves to full extension, roller wheels 94 and 96 roll along a segment of cam surfaces 102 and 104 and the increasing distance of cam surfaces 102 and 104 from shoulder 120 push roller wheels 94 and 96 further away from central joint 86. As can be seen in FIGS. 10a-d, this has the effect of pushing brace arms 28 and 30 around medial/lateral joints 82 and 84 toward leg 22 an angle θ. Brace arms 28 and 30 reach a maximum degree of inclination toward leg 22 when knee 26 is fully extended.

FIG. 4b depicts joint 24 as shown in FIG. 4a after adjustment wheel 92 has been partially adjusted to increase the bending force of brace 20 at full extension and shell 34 is inclined to an angle Φ which is less than 180°. FIG. 4c depicts joint 24 shown in FIGS. 4a and 5 but where adjustment wheel 92 has been adjusted to its maximum amount as shown by angle Φ which is less than angle Φ in FIG. 4b. In each figure, adjustment wheel 92 has been rotated clockwise to some extent so contact surfaces 120 on cams 88 and 90 are pushed further away from each other. This holds cam surfaces 102 and 104 closer to medial/lateral joints 82 and 84 respectively. As a result, wheels 94 and 96 contact cam surfaces 102 and 104 earlier as knee 26 moves to full extension and roll along a larger portion of cam surfaces 102 and 104. Consequently, brace arms 28 and 30 begin inclining toward leg 22 earlier as knee 26 extends and have a larger degree of inclination toward leg 22 at full extension than before adjustment wheel 92 was adjusted. Due to the symmetrical shape of adjustment wheel 92, cams 88 and 90 are always adjusted the same amount, which ensures that the bending force across the knee is even and patient discomfort due to an improperly adjusted brace 20 is minimized. However, adjustment wheel 92 may be asymmetrical if for some reason it is desirable that more force is applied by one of brace arms 28 and 30.

Figure 5:
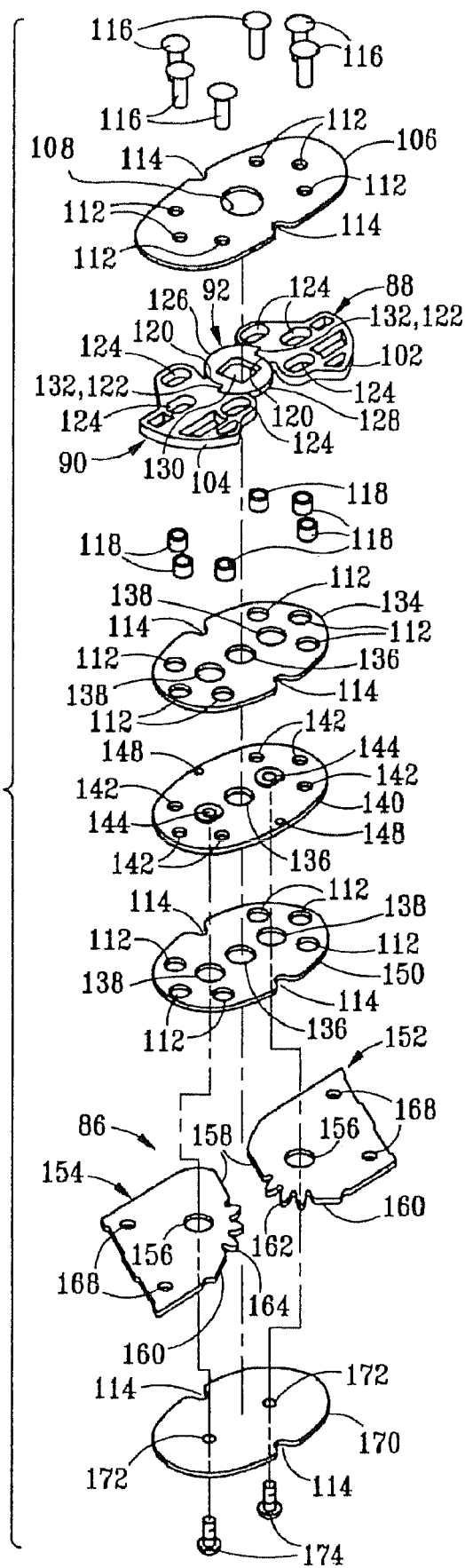
FIG. 5 is an exploded view of the central assembly of the preferred embodiment of the current invention.

As shown in FIG. 5, joint 24 is composed of many components. Base 106 is oval in shape and has a central opening 108 that knob 110 protrudes through and six holes 112 with three on each side of central opening 108 arranged in a triangular fashion. Base 106 also has notches 114 at either end of its central transverse axis. Pins 116 are seated in holes 112, have a hollow center, and extend from base 106. Bushings 118 are positioned over pins 116. Travel cams 88 and 90 are mirror images of each other and contain cam surfaces 102 and 104, contact surface 120, shoulder 122, and three slots 124. Pins 116 with bushings 118 fit in slots 124 of travel cam 88 and 90 to restrict travel cams 88 and 90 to a single linear motion. This keeps travel cams 88 and 90 properly aligned during use and adjustment of brace 20.

Adjustment wheel 92 fits between travel cams 88 and 90 and is made of two arcuate surfaces 126 and 128 around a central hole 130. Each arcuate surface 126 and 128 is a cam surface in the shape of a circle whose radius gets larger as you move along the surface. Shoulders 132 join arcuate surface 126 and 128 together where the radius of one arcuate surface is largest and the radius of the adjacent arcuate surface is at its smallest. Adjustment wheel 92 has 180° rotational symmetry so that for all diameters of adjustment wheel 92, arcuate surfaces 126 and 128 are equidistant from the center of star cam 92. This ensures that travel cams 88 and 90 are the same distance from the center of adjustment wheel 92, regardless of its rotational position. Knob 110 engages adjustment wheel 92 through central hole 130. Central hole 130 is in the shape of a square with a corner cut off to allow knob 110 to engage central hole 130 and rotate adjustment wheel 92 while ensuring that knob 110 is installed in the correct orientation.

Contact surfaces 120 of travel cams 88 and 90 seat on arcuate surfaces 126 and 128 respectively of adjustment wheel 92. As can be seen in FIG. 4a-c, as adjustment wheel 92 is rotated, the portion of arcuate surfaces 126 and 128 that abut against contact surfaces 120 becomes further away from the center of adjustment wheel 92. This results in travel cams being pushed further away from the center of adjustment wheel 92 in the only direction that slots 124 allow. This pushes cam surfaces 102 and 104 closer toward medial/lateral joints 82 and 84 respectively. Shoulders 132 on adjustment wheel 92 contact shoulders 122 on both travel cams to prevent adjustment wheel 92 from rotating directly from arcuate surfaces 126 and 128 being at their closest to the center of adjustment wheel 92 to being at their furthest distance.

Spacer plate 134 is oval in shape, has a shorter longitudinal axis than base 106, and has six holes 112 that seat over pins 116 and bushings 118. Spacer plate 134, along with base 106 ensures that adjustment wheel 92 and travel cams 88 and 90 all remain in the same plane. Spacer plate 134 also has notches 114 at either end of its transverse axis that are aligned with notches 114 in base 106, central hole 136 aligned with central opening 108 in base 106, and offset holes 138 along the longitudinal axis of spacer plate 134 on either side of central hole 136. Central hole 136 allows the end of knob 110 to pass through spacer plate 134. On top of spacer plate 134 is inner plate 140.

Inner plate 140 is also the same size and shape as spacer plate 134. It has six holes 142 that are aligned with holes 112 of spacer plate 134. However, holes 142 are only large enough for pins 116 so inner plate 140 rests on the top of bushings 118. Inner plate has hubs 144 located along its longitudinal axis and on either side of central hole 136. Hubs 144 extend above and slightly below inner plate 140 and seat within offset holes 138 of spacer plate 134. Hubs 144 also are internally threaded. Inner plate 140 has holes 148 that line up with notches 114 on spacer plate 134 and base 106. The end of hollow pins 116 is bent radially outward and back against the surface of inner plate 140, which keeps pins 116 from falling out of joint 24. A second spacer plate 150 that is identical to spacer plate 134 is located on the other side of inner plate 140. Offset holes 138 in spacer plate 150 seats over hubs 144 and holes 112 seat over the ends of pins 116 that have been bent radially outward.

Central joint 86 is located on top of second spacer plate 150. Central joint 86 is preferably in the form of a geared polycentric joint, although one of skill in the art will understand that the many other types of joints capable of allowing the knee joint to pivot may be used instead. Central joint 86 is made up of hinge member 152 and hinge member 154. Hinge members 152 and 154 each have opening 156, which allows hubs 144 to pivotally connect hinge members 152 and 154 to the rest of joint 24. As can be better seen in FIG. 6, hinge member 152 is connected to medial/lateral joint 82 using rivets 166 through holes 168 and hinge member 154 is likewise connected to medial/lateral joint 84. Gear teeth 162 and 164 on hinge members 152 and 154, respectively, mesh together to ensure that hinge members 152 and 154 rotate together.

Hinge members 152 and 154 also both have shoulders 158 and 160 that define the limits of rotation of hinge members 152 and 154 around hubs 144 and ultimately the flexion and extension limits of knee 26. Shoulders 158 on hinge members 152 and 154 abut each other to prevent central hinge 86 from rotating beyond the full extension of knee 26. Similarly, shoulders 160 on hinge members 152 and 154 abut each other to provide a limit to the rotation of central joint 86 in the other direction that does not prevent knee 26 from achieving a fully flexed position. Thus shoulders 158 and 160 allow knee 26 to undergo its full range of motion while helping to ensure that gear teeth 162 and 164 on hinge members 152 and 154 remain engaged. Shoulders 158 and 160 can also be positioned to restrict the range of motion of knee 26 as desired.

Figure 6:
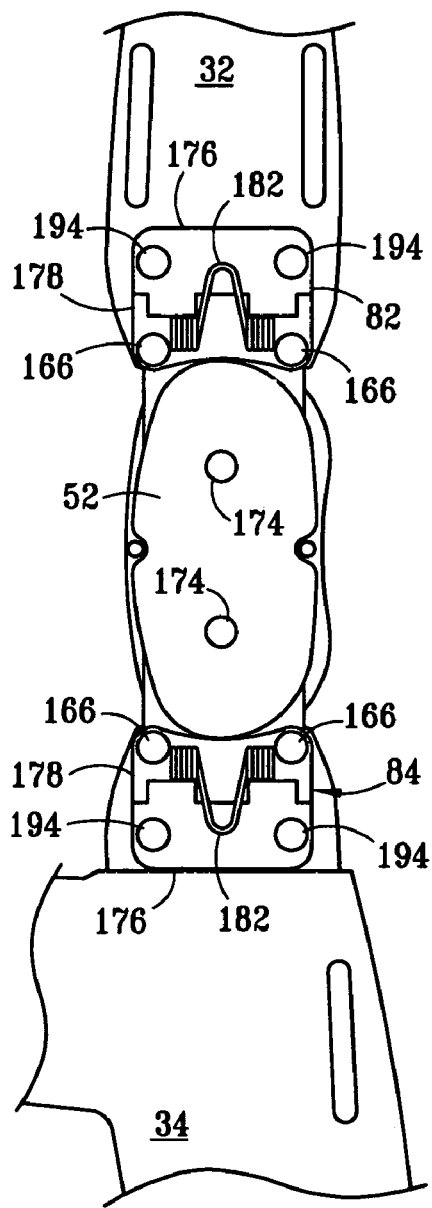
FIG. 6 is a plan view of the inside of the brace of the preferred embodiment showing the central joint and the medial/lateral joints.
Figure 7:
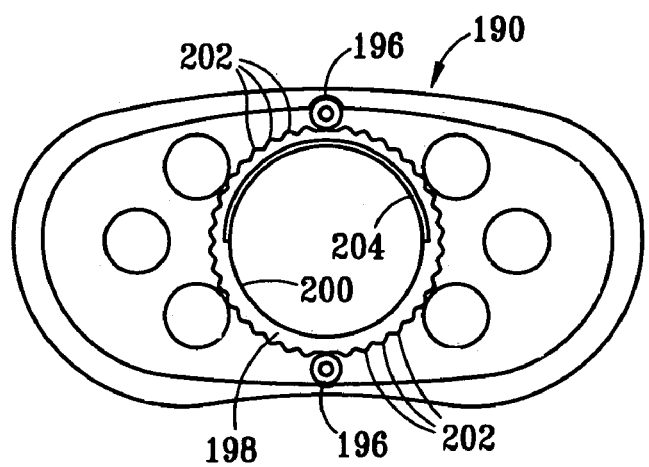
FIG. 7 is a bottom plan view of the cover of the joint of the preferred embodiment.

Plate 170 is seated on top of hinge members 152 and 154 so that they do not come off hubs 144. Plate 170 is the same shape as spacer plates 134 and 150 and also contains notches 114. Plate 170 contains offset holes 172 along its longitudinal axis that are smaller than and line up with hubs 144. Screws 174 pass through offset holes 172 and thread into inner thread section 146 in hubs 144 to hold plate 170 and hinge members 152 and 154 to inner plate 140 and the rest of joint 24. As seen in FIG. 6, hook strip 52 is located on the side of plate 170 opposite from joint 24 to secure kneepad 80 to the inside of joint 24.

Housing 190 is placed over base 106 and around joint 24. Screws are used to secure inner plate 140 to housing 190 through holes 148, notches 114 in spacer plate 134 and base 106 and into posts 196 in housing 190. As can be more clearly seen in FIG. 9, housing 190 has a central hole 198 in its center for knob 110. Around the edge of central hole 198 is channel 200 that holds knob 110 in joint 24. Regularly spaced around rim 200 are notches 202. Notches 202 do not extend entirely around channel 200 but are divided into two sections by posts 196. In addition, groove 204 runs along slightly less than halfway around channel 200.

Figure 8:
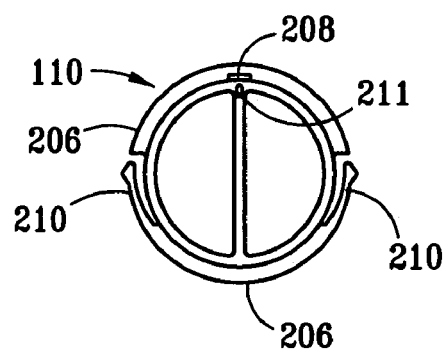
FIG. 8 is a top plan view of the adjustment knob of the preferred embodiment.
Figure 9:
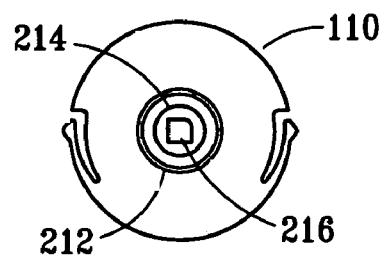
FIG. 9 is a bottom plan view of the adjustment knob of the preferred embodiment.

As can be more clearly seen in FIGS. 8 and 9, knob 110 has rim 206 that can seat in channel 200 of housing 190. There is also a projection 208 on the top of rim 206 that seats in groove 204. In this manner, projection 208 keeps knob 110 in a defined range so that star cam 92 is not rotated so far that contact surface 120 on travel cams 88 and 90 go off the end of shoulders 132 on star cam 92. Knob 110 also has fingers 210 that are resiliently biased to extend beyond the radius of rim 206 but are selectively deformable to compress within the radius of rim 206. Fingers 210 seat in notches 202 located in channel 200. As knob 110 is turned, fingers 210 are pushed radially inward by the wall of channel 200 and spring back to their original position in the next notch 202. This allows knob 110 to be moved, and correspondingly joint 24 to be adjusted, in discrete increments that can both be heard as well as felt by the person making the adjustment. In addition, it allows pointer 211 on knob 110 to line up with markings (not shown) on the top of housing 190 so that the adjustment position of the brace can be quickly determined. The lack of notches 202 by posts 196 also help to keep knob 110 in the desired range.

As shown with respect to FIG. 10, the back of knob 110 has a central column 212 that extends into joint 24. Cylinder 214 seats in central opening 108 in base 106 and allows knob 110 to freely rotate. Block 216 seats in central hole 130 of adjustment wheel 92. Block 216 is square in shape with one corner rounded off. The straight sides of block 216 allows knob 110 to rotate adjustment wheel 92 along with it while the curved corner ensures that knob 110 is seated in the desired orientation.

With respect to FIG. 6, brace arms 28 and 30 are connected to joint 24 by medial/lateral joints 82 and 84 respectively. Medial/lateral joints 82 and 84 are simple wrap hinges composed of two hinge wraps 176 and 178 joined by a hinge pin. Springs 182 are secured to hinge member 152 and 154 by rivets 166 that are also used to secure hinge member 152 and 154 to hinge wraps 178 of medial/lateral joints 88 and 90. Similarly, push blocks 98 and 100 are secured to brace arms 88 and 90 respectively using rivets 194 that also secure brace arms 88 and 90 to hinge wrap 178 of medial/lateral joints 88 and 90. Wheels 94 and 96 are pivotally connected to push blocks 98 and 100, respectively, and cover 184 secured over frame 182 and to brace arms 88 and 90 by rivets 194.

Springs 182 are not required for brace 20 to function, but are included in order to keep brace arms 28 and 30 from flopping too much, especially while the brace is being applied. This makes brace 20 appear less flimsy and more appealing to the patient. Medial/lateral joints 82 and 84 allow brace arms 28 and 30 to freely incline in both the medial and lateral directions. The travel cams 88 and 90 only restrict the inclination of brace arms 28 and 30 in a single direction, which is away from the leg when the brace is being worn. When adjusted to the lowest setting, as would be done when applying the brace, travel cams 88 and 90 restrict the movement of brace arms 28 and 30 to the least extent, providing the largest range of motion for brace arms 28 and 30 to flop around without any control over their inclination. However, this freedom of movement of brace arms 28 and 30 does not interfere with the function of the brace. As knee 26 moves to full extension, joint 24 pushes brace arms 28 and 30 against leg 22, preventing movement in the medial/lateral plane in the direction away from leg 22.

It is contemplated that brace 20 can be used in the following manner. The appropriate brace 20 is selected so that joint 24 is next to the damaged compartment of knee 26 that needs to be opened, which in this case is the left medial compartment. If desired, an undersleeve (not shown) may be placed on the leg to reduce slippage between brace 20 and leg 22. Joint 24 should be adjusted to its lowest setting so that brace arms 28 and 30 are not inclined at all when brace 20 is fully extended. This is accomplished by turning knob 110 clockwise until shoulders 132 on star cam 92 contact shoulders 122 on travel cams 88 and 90. The ends of straps 46, 48, 60, and 62 are removed from brace 20 and strap 62 is removed from D-ring 64 so that the front of brace 20 is open. In a seated position with the knee at approximately a 90° angle, brace arms 28 and 30 are placed against leg 22 with joint 24 lined up with knee 26. The center of kneepad 80 should be aligned over the adductor tubercle on the inside of knee 26.

Strap 46 is passed behind leg 22 and the end of web 63 is secured to pile surface 54 on finger 40. The other end of strap 46 is then removed and repositioned on strap 46 while applying tension to provide a secure fit around leg 22. Strap 46 should be snug but not so tight as to cause discomfort or affect circulation. After strap 46 is adjusted, it can be removed and reattached just by using the connection between web 63 and pile surface 54 on finger 40, thereby avoiding the need for adjustments every time the brace is applied. Next, strap 48 is passed behind leg 22 and the end of strap 48 is secured to pile surface 54 on finger 42. If adjustment to the length of strap 48 is required, the back end of strap 48 can be removed from itself and reattached to strap 48 in the desired location so that strap 48 is the desired length and fits leg 22 snugly. Similarly, after strap 48 has been adjusted, it can be removed and reattached by using the connection between the end of strap 48 and pile surface 54 on finger 42.

Then strap 62 is passed behind leg 22. While manually pushing bottom of extension 38 against leg 22, strap 62 is secured onto hook strip 52 on the bottom of extension 38. Then the free end of strap 62 is passed through D-ring 64, tensioned, and secured back onto strap 62 in front of leg 22. Strap 60 is then passed around the back of leg 22 and the end of strap 60 is secured to pile surface 54 on wrap 36. If the length of strap 60 needs to be adjusted, then the rear end of strap 60 can be released from itself by slot 66 and readjusted to shorten or lengthen strap 60 as required. After adjusting strap 60, it can be removed and reattached by using the connection between the free end of strap 60 and pile surface 54 on wrap 36. At this point, the patient should get up and walk around to ensure that brace 20 is comfortable and that there is no pinching or binding. If any adjustments need to be made, it is preferred that they also are made in the seated with knee 26 flexed at about 80-90°.

When brace 20 is properly located on leg 22, and while still in a seated position with the knee flexed at 80-90°, joint 24 is adjusted to generate the required bending force to provide the desired level of pain relief. Knob 110 should be adjusted counterclockwise one or two notches. As knob 110 is adjusted, fingers 210 will snap into successive notches 202. This allows joint 24 to be adjusted in discrete intervals. In addition, the movement of fingers 210 between notches 202 can be felt as well as produces an audible click in order to make it easy to keep track of the amount of adjustment that has been made. After adjusting knob 110 so that fingers 210 move over one or two notches 202, the patient should stand up and walk around to quantify the pain relief. If more unloading is required to obtain pain relief, then the patient should sit back down and adjust knob 110 so fingers 210 move around another one or two notches 202 around channel 200. If too much unloading is provided, brace 20 will become uncomfortable. Joint 24 should be adjusted to a point that maximizes the unloading the damaged compartment of knee 26 while minimizing any discomfort created by brace 20. Joint 24 should only be adjusted in an unloaded position with knee 26 bent enough so that roller wheels 94 and 96 do not contact cam surfaces 102 and 104. This can be assured by only adjusting the brace while in the seated position and with knee 26 at an approximately 90° angle.

The above descriptions of certain embodiments are made for the purposes of illustration only and are not intended to be limiting in any manner. Other alterations and modifications of the preferred embodiment will become apparent to those of ordinary skill in the art upon reading this disclosure, and it is intended that the scope of the invention disclosed herein be limited only by the broadest interpretation of the appended claims to which the inventor is legally entitled.

What is claimed is:

1. A dynamic brace comprising:
   an upper and a lower brace arm;
   at least one strap securing said brace arms to a leg;
   a central joint pivotally connecting said brace arms to allow said brace arms to pivot from a flexed to an extended position;
   a medial/lateral joint in each brace arm proximate to said central joint;
   two cams disposed between said medial/lateral joints, each said cam having first and second ends, an arcuate cam surface at said first end proximate to one of said medial/lateral joints, and a contact surface at said second end;
   said cams positioned so there is a distance between said cam surface and said medial/lateral joint;
   a stop block proximate to said medial/lateral joint in each brace arm and opposite from said arcuate cam surface, said stop block adapted to contact and slide along a segment of said cam surface, as said brace arms pivot from said flexed to said extended position;
   wherein each said cam surface is shaped such that as said stop block slides along said segment of said cam surface, said brace arm is dynamically inclined an amount toward said leg;
   wherein the length of said segment determines said amount said brace arms are dynamically inclined;
   an adjustment wheel disposed between said contact surfaces of said cams, said wheel adapted to equally adjust said distance of said cams from said medial/lateral joints;
   wherein said stop blocks slides along a longer segment of said cam surfaces when said cams are closer to said medial/lateral joints.

2. The brace of claim 1 further comprising a wheel in said stop block, wherein said stop block slides along said segment of said arcuate cam surface by said wheel rolling along said segment.

3. The brace of claim 1 wherein said central joint is a geared polycentric joint.

4. The brace of claim 1 wherein each said cam further comprise at least one slot axially aligned between said first and second ends of said cams and wherein pins seat in said slots to allow said distance between said cam surface and said medial/lateral joint to be adjusted.

5. The brace of claim 1 wherein said stop block does not contact said cam surface when said brace arms are in said flexed position.

6. A brace of claim 1 wherein said adjustment wheel comprises a central aperture and two surfaces, each surface contacting said contact surface on one of said cams, wherein said surfaces on said adjustment wheel have an arcuate shape such that, as said adjustment wheel is rotated in a first direction said cams are both equally pushed radially outward toward said medial/lateral joints, and as said adjustment wheel is rotated in a second direction said cams are both equally allowed to move radially inward away from said medial/lateral joints.

7. The brace of claim 6 further comprising:
a knob, located in a housing and adapted to rotate said adjustment wheel;
an indicator on said knob adapted to line up with index markings on said housing;
a cirumference in housing around said knob, said circumference containing regularly spaced detents;
at least one resiliently deformable finger protruding from said knob and adapted to seat in any of said plurality of detents.

8. The brace of claim 1 further comprising a shell secured to each brace arm and extending partially around the leg.

9. The brace of claim 8 wherein said shells are integral with said brace arm.

10. The brace of claim 1 further comprising at least one pad secured to said brace adapted to contact said leg.

11. The brace of claim 1 further comprising a spring spanning each medial/lateral joint biasing said brace arms to a non-inclined position.

12. A dynamic brace comprising:
an upper and a lower brace arm;
at least one strap securing each said brace arm to upper and lower portions of a leg;
a central joint pivotally connecting said brace arms to allow said brace arms to pivot from a flexed to an extended position;
a medial/lateral joint in each brace arm proximate to said central joint;
two cams disposed between said medial/lateral joints, each said cam having first and second ends, an arcuate cam surface at said first end proximate to one of said medial/lateral joints, and a contact surface at said second end;
said cams positioned so there is a distance between said cam surface and said medial/lateral joint;
a stop block proximate to said medial/lateral joint in each said brace arm, opposite from said cam surface;
a wheel pivotally connected in said stop block adapted to roll along a segment of said cam surface as said brace arms pivot from said flexed to said extended position;
wherein each said cam surface is shaped such that as said wheel rolls along said segment of said cam surface, said brace arm is dynamically inclined an amount toward said leg;
wherein the length of said segment determines said amount said brace arms are dynamically inclined as said brace arms reach said extended position;
wherein said wheel rolls along a longer segment of said cam surfaces when said cams are closer to said medial/lateral joints;
an adjustment wheel disposed between said contact surfaces of said cams;
said adjustment wheel comprising a central aperture and two cam surfaces, each surface contacting said contact surface on one of said cams and having an arcuate shape such that as said adjustment wheel is rotated in a first direction, said cams are equally pushed radially outward toward said medial/lateral joints and as said adjustment wheel is rotated in a second direction, said travel cams are equally allowed to move radially inward away from said medial/lateral joints.

13. The brace of claim 12 wherein said central joint is a geared polycentric joint.

14. The brace of claim 13 wherein said cams further comprise at least one slot axially aligned between said first and second ends of said cams and wherein pins seat in said slots to allow said distance between said cam surface and said medial/lateral joint to be adjusted.

15. The brace of claim 14 further comprising:
a knob, located in a housing and adapted to rotate said adjustment wheel;
an indicator on said knob adapted to line up with index markings on said housing;
a circumference in said housing around said knob, said circumference containing regularly spaced detents;
at least one resiliently deformable finger protruding from said knob and adapted to seat in any of said plurality of detents.

16. The brace of claim 12 further comprising a shell secured to each brace arm and extending partially around the leg.

17. The brace of claim 16 wherein said shells are integral with said brace arms.

18. The brace of claim 12 further comprising at least one pad secured to said brace adapted to contact said leg.

19. The brace of claim 12 further comprising, a spring spanning each medial/lateral joint biasing said brace arms to a non-inclined position.

20. The brace of claim 12 further comprising:
wherein said central joint is a geared polycentric joint;
at least one slot axially aligned between said first and second ends of said cams;
pins seated in said at least one slot in said cams to allow said distance between said cam surface and said medial/lateral joint to be adjusted;
a knob, located in a housing and adapted to rotate said adjustment wheel;
an indicator on said knob adapted to line up with index markings on said housing;
a circumference in said housing around said knob, said circumference containing regularly spaced detents;
at least one resiliently deformable finger protruding from said knob and adapted to seat in any of said plurality of detents;
a shell secured to each brace arm and extending partially around the leg;
at least one pad secured to said brace and adapted to contact said leg;
a spring spanning each medial/lateral joint biasing said brace arms to a non-inclined position.

21. A dynamic brace comprising:
an upper and a lower brace arm;
at least one strap securing said brace arms to a leg;
a central joint pivotally connecting said brace arms such that said brace arms can pivot from a flexed to an extended position;
a medial/lateral joint in each said brace arm proximate to said central joint;
cam means for dynamically inclining said brace arms an amount toward said leg as said brace arms move to said extended position;
adjustment means for adjusting said amount of inclination of each brace arms in said extended position;
wherein said amount of inclination is equal for each said brace arm.

22. The brace of claim 21 wherein said cam means equally inclines said brace arms an amount toward said leg.

23. The brace of claim 21 wherein said adjustment means is adjusted to relieve pain associated with unicompartmental osteoarthritis.

24. The brace of claim 21 wherein said cam means comprises:
- two cams disposed between said medial/lateral joints, each said cam having first and second ends, an arcuate cam surface at said first end facing one of said medial/lateral joints, and a contact surface at said second end;
- a stop block proximate to the medial/lateral joint in each brace arm, opposite from said cam surface, and adapted to slide along a segment of said cam surface as said brace arms move to said extended position;
- wherein as said stop block slides along said segment of said cam surface said brace arms are inclined an amount toward said leg.

25. The brace of claim 24 wherein said adjustment means increases said amount of inclination by adjusting said cams such that said stop block slides along a longer segment of said cam surface.

26. The dynamic brace of claim 24 wherein said cam means further comprises a wheel pivotally connected to each said stop block, wherein said stop block slides along said segment by said wheel rolling along said segment.

27. The brace of claim 26 wherein said adjustment means comprises an adjustment wheel disposed between said cams and carries out said adjustment by adjusting the distance between said cams and said medial/lateral joints.

28. The brace of claim 27 wherein said adjustment wheel comprises a central aperture and two cam surfaces, each surface adapted to contact one of said cams such that when said adjustment wheel is rotated, said cams are equally pushed radially outward away from said adjustment wheel or equally allowed to move radially inward toward said adjustment wheel.

29. The brace of claim 24 wherein said central joint comprises a geared polycentric joint.

30. A method of applying a dynamic bending force to a leg comprising:
- locating a brace around a leg, said brace comprising an upper and a lower brace arm, a central joint positioned at a knee in said leg, said central joint pivotally connecting said brace arms such that said brace arms can pivot from a flexed to an extended position, a medial/lateral joint in each brace arm to allow said brace arm to incline toward the leg;
- dynamically inclining said brace arms an amount toward said knee as said brace moves from said flexed to said extended position to apply a bending force across said knee;
- adjusting said amount said brace arms are inclined in said extended position such that said bending force has a desired magnitude;
- wherein said adjusting step comprises a single adjustment that equally affects said amount of inclination of each brace arm.

31. The method of claim 30 wherein no bending force is applied when said brace arms are in said flexed position.

32. The method of claim 30 wherein said brace comprises cams that perform the dynamically inclining step.

33. The method of claim 32 wherein said bending force is used to treat unicompartmental osteoarthritis.

34. The method of claim 33 wherein said desired magnitude is sufficient to completely open a damaged compartment of a knee.

35. The method of claim 32 wherein said brace further comprises a central adjustment wheel that it used to carry out the adjustment step.

36. The method of claim 32 wherein said brace comprises two cams and said adjustment wheel is located between said cams and carries out the adjustment step by adjusting the distance between said cams and said medial/lateral joints.

37. The method of claim 36 wherein said brace further comprises a stop block in each brace arm adapted to contact and slide along a segment of said cam, thereby dynamically inclining said brace arms an amount toward said leg.

* * * * *